US012146846B2

United States Patent
Hisada et al.

(10) Patent No.: US 12,146,846 B2
(45) Date of Patent: Nov. 19, 2024

(54) CELL ANALYSIS APPARATUS AND CELL ANALYSIS METHOD

(71) Applicant: HITACHI HIGH-TECH CORPORATION, Tokyo (JP)

(72) Inventors: Akiko Hisada, Tokyo (JP); Yuusuke Oominami, Tokyo (JP); Yuji Matsumoto, Tokyo (JP); Takaaki Tsuchida, Tokyo (JP); Noriko Motoi, Tokyo (JP); Mizuho Fujima, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 939 days.

(21) Appl. No.: 17/271,825

(22) PCT Filed: Sep. 5, 2018

(86) PCT No.: PCT/JP2018/032823
§ 371 (c)(1),
(2) Date: Feb. 26, 2021

(87) PCT Pub. No.: WO2020/049642
PCT Pub. Date: Mar. 12, 2020

(65) Prior Publication Data
US 2021/0181127 A1   Jun. 17, 2021

(51) Int. Cl.
*G01N 23/2251* (2018.01)
*G01N 23/20091* (2018.01)
*G01N 23/2209* (2018.01)
*G01N 33/483* (2006.01)

(52) U.S. Cl.
CPC ... *G01N 23/2251* (2013.01); *G01N 23/20091* (2013.01); *G01N 23/2209* (2018.02); *G01N 33/4833* (2013.01)

(58) Field of Classification Search
CPC .......... G01N 23/2251; G01N 23/2209; G01N 23/20091; G01N 33/4833
See application file for complete search history.

(56) References Cited

U.S. PATENT DOCUMENTS

| 2012/0052491 | A1  | 3/2012 | Shioyama et al. |
| 2016/0084778 | A1  | 3/2016 | Kojima et al. |
| 2017/0192003 | A1* | 7/2017 | Kuhn ................. G01N 33/5743 |

FOREIGN PATENT DOCUMENTS

| JP | 2002-296205 A | 10/2002 |
| JP | 2010-008406 A | 1/2010 |
| WO | 2014/132383 A1 | 9/2014 |

OTHER PUBLICATIONS

Patai, K., et al., "Phosphor/sulphur ratio: An indicator of malignant uterus change," Oncology Research, 2005, vol. 15, No. 4, pp. 215-217.

(Continued)

*Primary Examiner* — Margaret G Mastrodonato
(74) *Attorney, Agent, or Firm* — Volpe Koenig

(57) ABSTRACT

Cancer is determined quantitatively, rapidly and highly accurately by using a cell specimen such as a tissue section or a smear preparation. More specifically, provided is a method and apparatus for analyzing the proliferating activity or malignancy of cells by measuring the signal intensity of phosphorus of cells or the signal intensities of phosphorus and sulfur of cells.

18 Claims, 5 Drawing Sheets

(56) References Cited

OTHER PUBLICATIONS

Bandura, D., et al., "Characterization of phosphorus content of biological samples by ICP-DRC-MS: Potential tool for cancer research," Journal of Analytical Atomic Spectrometry, 2004, vol. 19, No. 1, pp. 96-100.
Hare, D., et al., "Elemental bio-imaging of melanoma in lymph node biopsies," The Analyst, 2009, vol. 134, No. 3, pp. 450-453.
Sikora, R., et al., "Measurement of BBN-induced alterations in rat urothelium by electron microscopic X-ray microanalysis," Urological Research, 1994, vol. 22, No. 3, pp. 167-170.
Chmura, L., et al., "Quantification of selected elements in ovarian tumors and their potentials as a tissue classifier," J. Physiol Pharmacol., Oct. 2017, vol. 68, No. 5, pp. 699-707.
Wandzilak, A., et al., "X-ray fluorescence study of the concentration of selected trace and minor elements in human brain tumors," Spectrochimica Acta Part B, 2015, vol. 114, pp. 52-57.

* cited by examiner

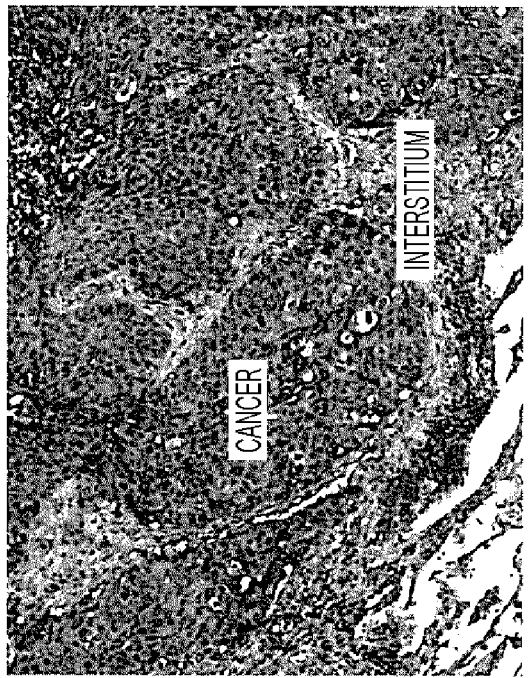
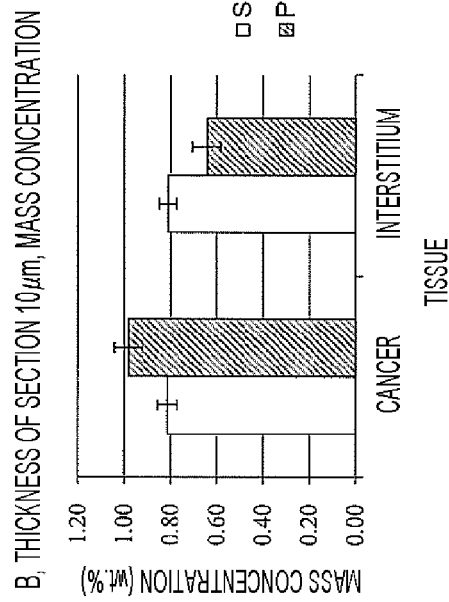
FIG. 5A
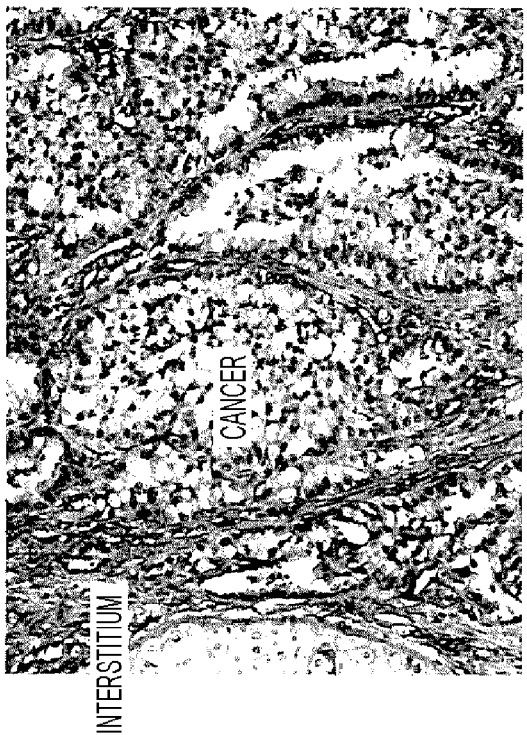
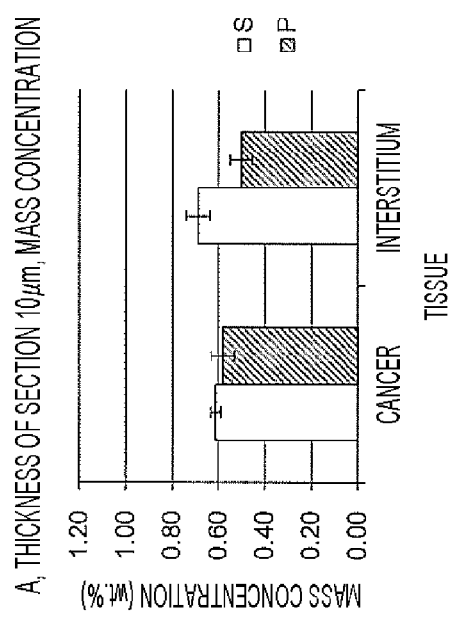
FIG. 5B

CELL ANALYSIS APPARATUS AND CELL ANALYSIS METHOD

TECHNICAL FIELD

The present invention relates to a cell analysis method and a cell analysis apparatus. More particularly, the present invention relates to a method and apparatus for analyzing the proliferating activity or malignancy of cells.

BACKGROUND ART

In the pathological examination for determining cancer, a tissue section or smear cells adhered to a slide glass is stained, then abnormality in the size, shape, arrangement, background or the like of cells is determined by observing the color and shape by the cytoscreener or pathologic diagnostician through optical microscope observation, and the determination result of the presence of cancer is reported. Various determination criteria are provided for eliminating variation caused by the subject of the observer.

However, in the actual pathologic diagnosis, the morphology of a diseased tissue such as cancer tissue is individually different. Thus, there is a case where it is difficult to determine cancer, and there are many cases where the diagnosis is different depending on the pathologist. Also, in general pathological preparations, substances contained in cells or tissues are stained with different dyes for discrimination, and therefore the difference between staining tests and the difference between facilities are also problematic. Thus, a technique for assisting determination of cancer has been required, and particularly, quantitative determination criteria which do not make difference due to human operation and facility have been required.

As a conventional method, a method and apparatus for analyzing the malignancy of cancer by subjecting DNA of cells to fluorescent staining and determining the fluorescence intensity of each cell by flow cytometry have been known as a technique for quantitatively analyzing cells (PTL 1).

However, in flow cytometry, the fluorescence intensity from the sample is measured by subjecting isolated cells to fluorescent staining and introducing a suspension of the stained cells into a flow cell. Therefore, there are problems that: a fresh tissue which has been excised by a highly invasive method such as surgery is required; a substantial amount of number of cells are required in consideration of the dead volume in order to introduce the cells into the flow cell; a specimen cannot be preserved because the cells after measurement are discarded; and a specimen must be prepared separately from routine operations such as preparation of a tissue section or smear cell which is a normal pathological specimen.

Meanwhile, although it is not intended for pathological examination, in the examination of cultured tissues for transplantation, a method and apparatus for quantitatively analyzing the characteristics of tissues by irradiating a tissue section with electron beams, detecting characteristics X-rays derived from elements contained in the tissue section by an X-ray detector to perform elemental analysis, and mapping the distribution of elements have been known (PTL 2). Furthermore, as one of the examples of an apparatus for performing elemental analysis on the surface of biological tissues regardless of the morphology of specimens including tissue sections and smear cells, a combination of a scanning electron microscope (SEM) and an energy dispersive X-ray spectrometry (EDX) elemental analysis has been known (PTL 3).

CITATION LIST

Patent Literature

PTL 1: US 2012/0052491 A1
PTL 2: JP 2002-296205 A
PTL 3: JP 2010-008406 A

SUMMARY OF INVENTION

Technical Problem

In view of the above-described problems in the field of pathology, the present invention provides a method and apparatus for quantitatively determining cancer rapidly and highly accurately in specimens such as tissue sections and smear cells.

Solution to Problem

The present inventor focused that one phosphorus atom is bound per one base of DNA, and in the DNA synthesis process before cell division, the number of phosphorus atoms derived from DNA increases in a proportional manner, measured the difference in the phosphorus amount for each cell or cell nucleus contained in a sample, and quantitatively detected the relative difference in the DNA amount for each cell or cell nucleus. As a result, the present inventor found that it is possible to analyze the proliferating activity of cells and the malignancy of tumor cells contained in the sample.

Also, the present inventor focused on sulfur which is a constitutional element of protein, and found that, in tissues having high cell division activity, the amount of cytoplasm or extracellular matrix is relatively small relative to the amount of cell nucleus in many cases, and therefore the cell proliferating activity in tissues and the malignancy of tumor cells can be analyzed by determining the concentration ratio of phosphorus contained in a large amount in cell nucleus and sulfur which is a constitutional element of protein and amino acid in cytoplasm and extracellular matrix.

In one aspect, provided is a method for analyzing a proliferating activity or malignancy of a cell, the method including: measuring a signal intensity of phosphorus for a sample containing a plurality of cells by electron beam or X-ray irradiation elemental analysis; and comparing a cell distribution according to the measured signal intensity of phosphorus of the sample with a cell distribution according to a signal intensity of a control.

In another aspect, provided is an apparatus for analyzing a proliferating activity or malignancy of a cell, the apparatus including: an element analysis unit that is configured to measure a signal intensity of phosphorus by electron beam or X-ray irradiation elemental analysis; a database to which a signal intensity of phosphorus of a control is registered; and a comparison unit that is configured to compare a cell distribution according to the signal intensity of phosphorus measured in the element analysis unit with a cell distribution according to the signal intensity of phosphorus of a control registered in the database.

In another embodiment, provided is a method for analyzing a proliferating activity of a cell or a malignancy of a tumor, the method including: measuring signal intensities of phosphorus and sulfur for a sample containing a plurality of cells or a sample containing a cell and an extracellular component such as extracellular matrix by electron beam or X-ray irradiation elemental analysis, and comparing a concentration ratio of phosphorus and sulfur calculated from the measured signal intensities of phosphorus and sulfur of the sample with a concentration ratio of phosphorus and sulfur of a control.

In another aspect, provided is an apparatus for analyzing a proliferating activity a cell or a malignancy of a tumor, the apparatus including: an element analysis unit that is configured to measure signal intensities of phosphorus and sulfur by electron beam or X-ray irradiation elemental analysis; a database to which signal intensities of phosphorus and sulfur or a concentration ratio of phosphorus and sulfur of a control are registered; and a comparison unit that is configured to compare a concentration ratio of phosphorus and sulfur calculated from the signal intensities of phosphorus and sulfur measured in the element analysis unit with a concentration ratio of phosphorus and sulfur of a control registered in the database.

Advantageous Effects of Invention

According to the present invention, a method and apparatus for analyzing the proliferating activity of cells or the malignancy of tumors are provided. The method and apparatus enable analysis of the proliferating activity and malignancy of cells rapidly and highly accurately by using, for example, a trace amount of cell specimen, such as expectoration, exfoliated cells in urine, scraped materials, tissue imprint preparations, or tissue preparations. Accordingly, such a method and apparatus allow quantitative determination of cancer, and are therefore useful in the medical field.

BRIEF DESCRIPTION OF DRAWINGS

FIG. 4A and FIG. 4B are histograms obtained by using human mesenchymal stem cells (hMSC), and FIG. 4C and FIG. 4D are histograms obtained by using cell lines derived from human cervical cancer (HeLa cells).

FIGS. 5A and 5B show an example of calculation of the concentration ratio of phosphorus and sulfur of the tissue by the cell analysis method.

DESCRIPTION OF EMBODIMENTS

Figure 1:
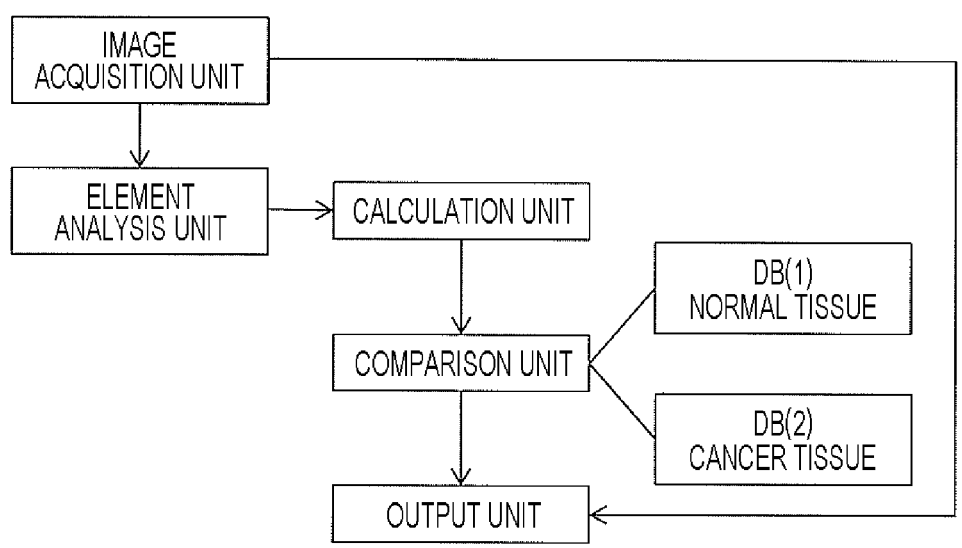
FIG. 1 is a diagram illustrating a configuration example of a cell analysis apparatus.

The present disclosure relates to a method for analyzing the proliferating activity or malignancy of cells (herein also referred to as "cell analysis method), and an apparatus for analyzing the proliferating activity or malignancy of cells (herein also referred to as "cell analysis apparatus").

The proliferating activity of cells refers to the speed or degree that cells proliferate or double. The malignancy of cells is associated with high proliferating activity of cells. Also, tumor cells which exhibit the proliferating activity considerably different from normal cells, and tumor cells in which DNA per one cell exhibits abnormal increase than normal synthesis before division may be referred to as cells having high malignancy. The proliferating activity and malignancy of cells are a relative measure and can be determined for, for example, the proliferating activity and malignancy of normal cells (for example, it can be represented as a relative value in a case where the proliferating activity and malignancy of normal cells derived from the tumor is determined as 0 or 1, but this is not limited thereto) or the proliferating activity and malignancy of known tumor cells.

A sample to be analyzed may be any sample which contains a plurality of cells and in which analysis of the proliferating activity or malignancy of cells is desired, and is not limited. For example, the sample may be a sample derived from a subject (for example, an organ, a tissue, and a cell population), or may be a sample obtained by culturing (for example, a cell cluster, a cell population, a tissue). The subject may not be particularly limited as long as it is an organism, and includes animals, for example, mammals (primates including humans, pet animals, domestic animals, and the like), reptiles, birds, fish, plants, and bacteria.

The sample in which analysis of the proliferating activity or malignancy of cells is desired may be, for example, a sample in which determination is desired whether it includes cancer cells, a sample in which determination of the malignancy of cancer is desired, and the like, or a sample in which it is determined whether cells being cultured (for example, stem cells such as iPS cells) abnormally proliferate, and the like, but are not limited thereto.

In an embodiment, the subject may be mammals, for example, humans, and the sample may be a sample derived from the subject, or a sample obtained by culturing cells derived from the subject. Examples of the sample derived from the subject include, although not limited thereto, expectoration, exfoliated cells in urine, scraped materials (oral mucosa, urethra, and the like), blood (fraction including blood cells), tissue imprint preparations, organs, cell populations, and tissue sections.

The number of cells contained in the sample varies depending on the type of cell to be analyzed, the type of apparatus that performs elemental analysis, and the like. The number may be approximately 30 to 1,000, 30 to 500, 30 to 300, 30 to 200, 30 to 100, 40 to 200, 40 to 100, 50 to 200, and 50 to 100.

Figure 2:
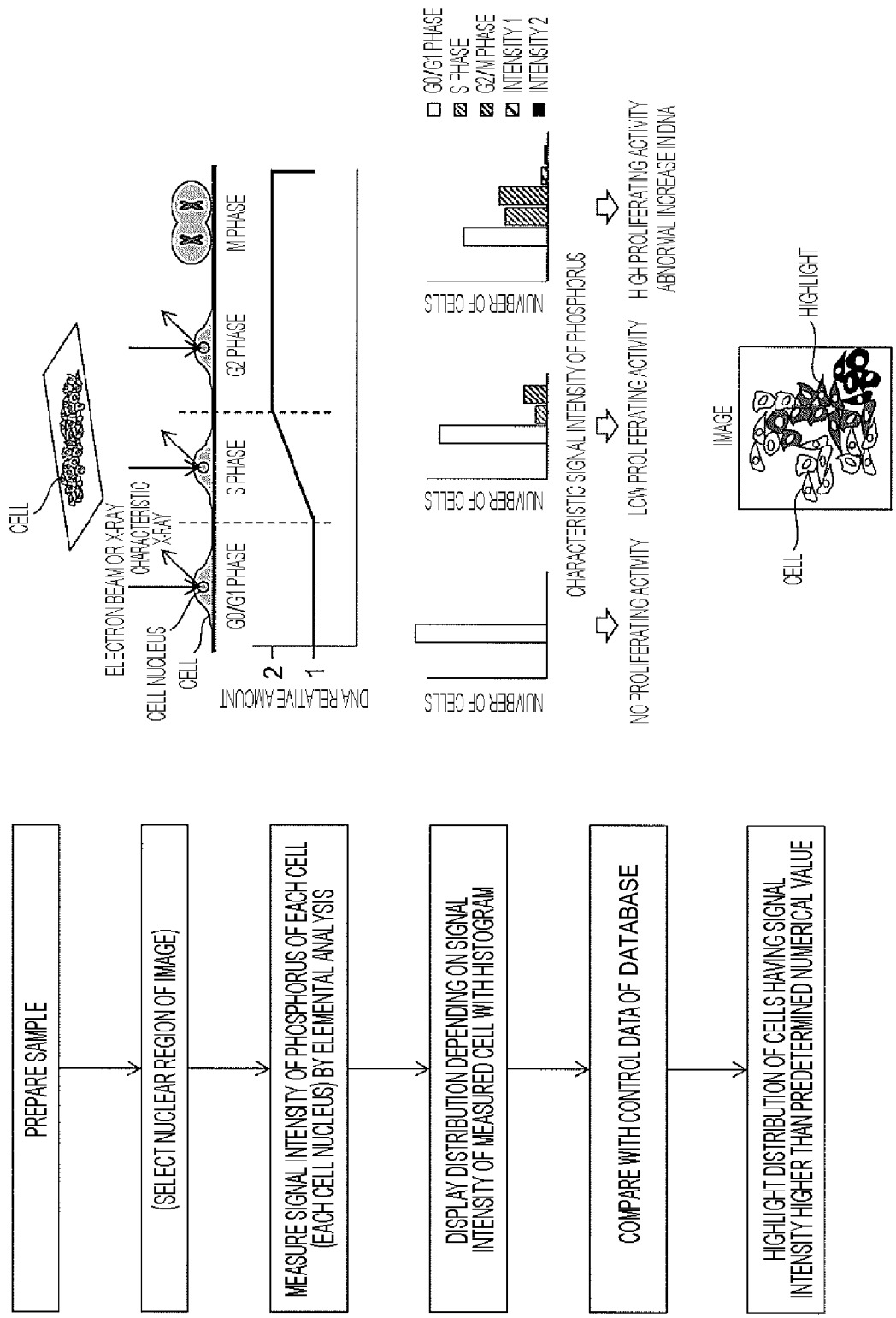
FIG. 2 shows an analysis flow chart and data display example according to one example of a cell analysis method.
Figure 3:
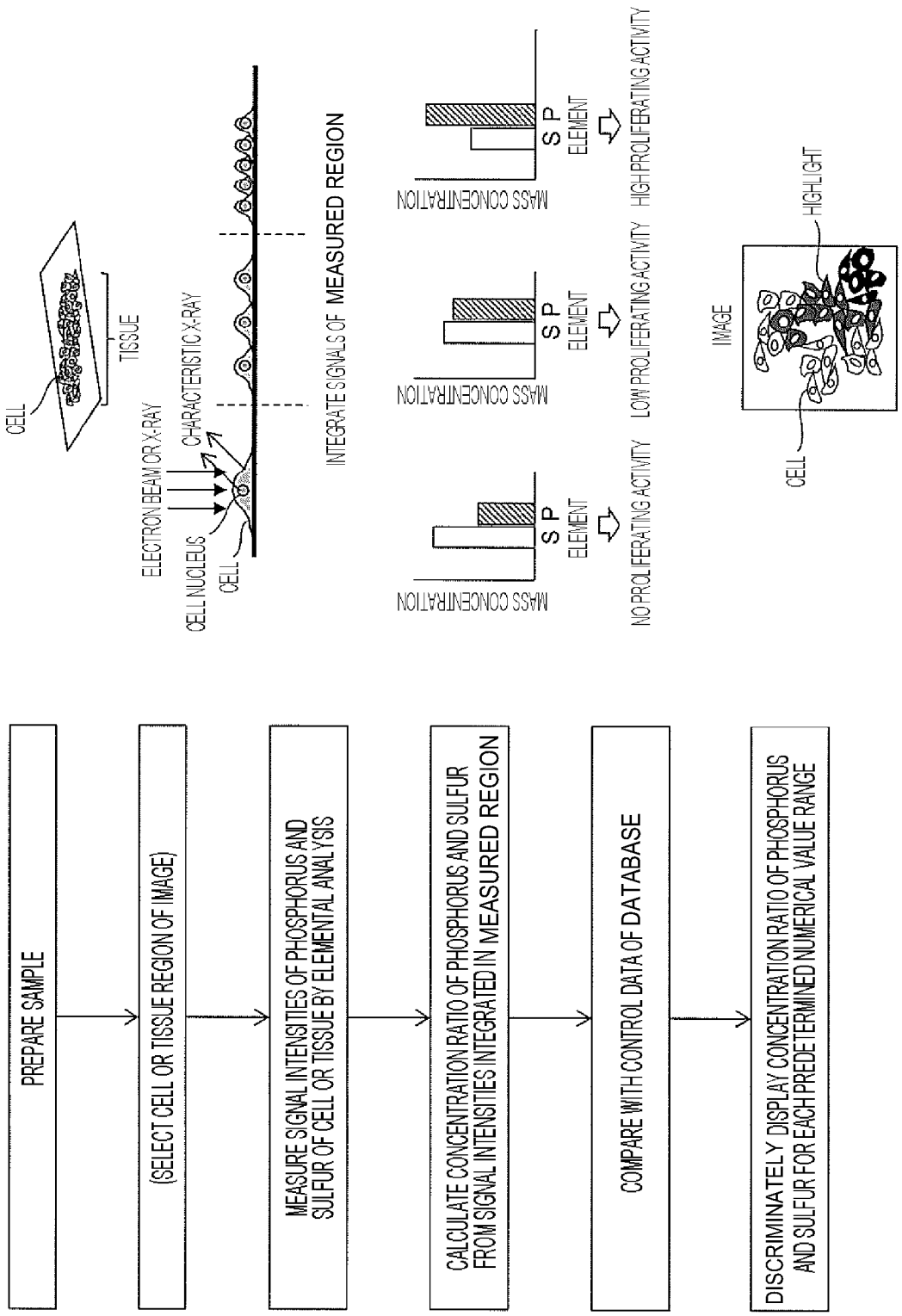
FIG. 3 shows an analysis flow chart and data display example according to another example of a cell analysis method.

The analysis process according to one example of the cell analysis method of the present disclosure is shown in FIGS. 2 and 3. First, a sample to be analyzed may be prepared. Preparation of the sample varies depending on the type of sample of the subject, the type of apparatus that performs elemental analysis, and the like, but preparation can be performed by methods commonly used in the technical field.

In a case of using electron beams for image acquisition and/or elemental analysis, it may be desirable to subject the sample to a treatment for preventing the sample from being significantly modified or deformed even when the sample is placed in a vacuum environment. For example, a tissue section or cells may be allowed to adhere to a supporting substrate such as a slide glass, and dried, then inserted in a sample chamber, and irradiated with electron beams in a vacuum environment.

In one aspect, the cell analysis method of the present disclosure may include: measuring a signal intensity of phosphorus for a sample containing a plurality of cells by electron beam or X-ray irradiation elemental analysis; and comparing a cell distribution according to the measured signal intensity of phosphorus of the sample with a cell distribution according to a signal intensity of a control.

In another embodiment, the cell analysis method of the present disclosure may include: measuring signal intensities of phosphorus and sulfur for a sample containing a plurality of cells or a sample containing cells and extracellular components such as extracellular matrix by electron beam or X-ray irradiation elemental analysis; and comparing a concentration ratio of phosphorus and sulfur calculated from the measured signal intensities of phosphorus and sulfur of the sample with a concentration ratio of phosphorus and sulfur of a control. Furthermore, the cell analysis method of the present disclosure may include calculating the concentration ratio of phosphorus and sulfur from the measured signal intensities of phosphorus and sulfur of the sample.

First, the signal intensity of phosphorus or the signal intensities of phosphorus and sulfur may be measured for a sample (each cell or region of cell) by electron beam or X-ray irradiation elemental analysis. The electron beam or X-ray irradiation elemental analysis is a method of irradiating a sample with electron beams or X-rays, detecting characteristics X-rays or fluorescent X-rays generated from the sample, thus analyzing the elemental composition corresponding the characteristics X-rays or fluorescent X-rays, and is a technique known in the technical field (for example, PTL 2 or 3). With this elemental analysis, the amount of phosphorus or the amounts of phosphorus and sulfur in a portion that has been irradiated with electron beams or X-rays can be measured. An element analysis unit used for elemental analysis includes an electron beam or X-ray irradiation unit and an X-ray detection unit. As the X-ray detection unit, for example, an energy dispersive X-ray spectroscope (EDS) or a wavelength-dispersive X-ray spectroscope (WDS) can be used for detecting characteristics X-rays generated by electron beam irradiation, or for example, an X-ray microscope can be used for detecting fluorescent X-rays generated by X-ray irradiation.

More specifically, a sample may be irradiated with electron beams or X-rays from the electron beam or X-ray irradiation unit, and measurement of characteristics X-rays or fluorescent X-rays for phosphorus may be performed in the X-ray detection unit (FIG. 2). As the quantitative value of phosphorus for each cell or each nucleus, the integrated value of characteristics X-ray signals within a measurement time, the value of the characteristics X-ray signal per unit time, or the mass concentration calculated in a case where any element(s) is selected may be obtained. Here, it may be important to determine the signal intensity of phosphorus, not for the entire sample, but for each cell or each cell nucleus.

In another embodiment, more specifically, a sample may be irradiated with electron beams or X-rays from the electron beam or X-ray irradiation unit, and measurement of characteristics X-rays or fluorescent X-rays for phosphorus and sulfur may be performed in the X-ray detection unit (FIG. 3). As the quantitative values of phosphorus and sulfur for each cell, or cell population, or tissue (region of cell) containing cells and extracellular components such as extracellular matrix, the integrated value of characteristics X-ray signals within a measurement time, the value of the characteristics X-ray signal per unit time, or the mass concentration calculated in a case where any element(s) is selected may be obtained. Here, the signal intensities of phosphorus and sulfur, not for cell nucleus, but for each cell, or each cell population, or each continuous tissue (region of cell) containing cells and extracellular components such as extracellular matrix may be determined.

The cell analysis method may optionally further include a step of acquiring a scanning electron microscope (SEM) image of the sample. By acquiring the SEM image of the sample, it becomes possible to select the nuclear region of the cell and analyze the morphology of the cell, and the like.

In an embodiment, the cell analysis method may further include: a step of acquiring a scanning electron microscope (SEM) image of the sample before the signal intensity of phosphorus is measured; and a step of selecting a nuclear region of the cells from the SEM image, and thereafter, the signal intensity of phosphorus in the selected nuclear region is measured. When an image of the sample is acquired by using an SEM, an observation magnification at which the cell nucleus can be identified is desired, and an appropriate magnification may be adjusted depending on the type of the cell. The observation magnification may be approximately 100 to 1,000, but is not limited thereto. An SEM image in any selected area is acquired, and then a region of the nucleus of the cell in the visual field may be selected.

In an embodiment, the cell analysis method may further include: a step of acquiring a scanning electron microscope (SEM) image of the sample before the signal intensities of phosphorus and sulfur are measured; and a step of selecting a region of the cells from the SEM image, and thereafter, the signal intensities of phosphorus and sulfur in the selected region of the cells are measured. The observation magnification of the SEM is as described above.

The cell analysis method may optionally include a step of staining a sample and observing the sample by an optical microscope. With this step, it becomes possible to analyze the nuclear region of the cell and analyze the state of the cell. Staining of the sample can be performed by using dyes known in technical field. Examples of such dyes include hematoxylin, hematoxylin-eosin, a May-Giemsa staining solution, methylene blue, safranin, and toluidine blue, or fluorescent dyes such as DAPI (4',6-diamidino-2-phenylindole), and propidium iodide (PI), but are not limited thereto.

In an embodiment, the cell analysis method may further include a step of staining a sample and observing the sample by an optical microscope before the step of acquiring an SEM image, and a step of selecting a region in which an image of the sample is acquired, and thereafter, an SEM image in the selected region is acquired.

Elemental analysis may be performed for a plurality of visual fields (optionally acquiring an image) in the same manner by repeating the above operation, and the relative quantitative value of phosphorus for each cell or nuclear region may be obtained. Alternatively, the concentration ratio of phosphorus and sulfur for each cell, cell population, or continuous tissue containing cells and extracellular components such as extracellular matrix may be obtained. The total number of measured cells may be desirably at least 50 cells, but is not limited thereto.

Subsequently, in the cell analysis method of the present disclosure, the cell distribution according to the measured signal intensity of phosphorus of the sample may be compared with the cell distribution according to the signal intensity of the control. The cell distribution according to the signal intensity of phosphorus refers to a distribution indicating the number of cells in a predetermined range of signal intensity of phosphorus for each range of signal intensity, and can be represented by a histogram (for example, right side in FIG. 2).

In another cell analysis method of the present disclosure, the concentration ratio of phosphorus and sulfur may be calculated from the measured signal intensities of phosphorus and sulfur of the sample, and then compared with the concentration ratio of phosphorus and sulfur of the control sample.

Any control may be used as long as it can be compared in the analysis of the proliferating activity and malignancy of the cell. For example, at least one type selected from the group consisting of normal cells, malignant cells, cells having high proliferating activity, and cells exhibiting abnormal DNA increase can be used. The control cell may be a cell derived from a subject which is the same as the subject of the sample, or a cell derived from a subject which is different from the subject of the sample, but may preferably be a cell derived from the same species (for example, humans). Also, the control cell may preferably be a cell derived from a source which is the same as the sample (for example, the same organ or cell population).

The signal intensity of phosphorus or the signal intensities of phosphorus and sulfur of the control may be measured at the same time or approximately the same time as measurement of the sample, or may be measured in advance. The signal intensity of phosphorus or the signal intensities of phosphorus and sulfur of the control which has been pre-measured may be one registered in a database.

For example, in a case where the control contains normal cells, the cell distribution according to the signal intensity of phosphorus of the normal cell may be the cell distribution according to the signal intensity of phosphorus, obtained by similarly measuring normal cells prepared from an organ or cell population same as that of the sample. Alternatively, the cell distribution according to the signal intensity of phosphorus of the normal cell may be the cell distribution according to the signal intensity of phosphorus of normal cells derived from an organ or cell population of the same species which is different from the sample.

For example, in a case where the control contains normal cells, the concentration ratio of phosphorus and sulfur of the normal cell may be the concentration ratio of phosphorus and sulfur, obtained by similarly measuring normal cells prepared from an organ or cell population which is the same as that of the sample. Alternatively, the concentration ratio of phosphorus and sulfur of the normal cell may be the concentration ratio of phosphorus and sulfur of normal cells derived from an organ or cell population of the same species which is different from the sample.

In an embodiment, in a case where the control contains normal cells, the cell analysis method may include steps of comparing to the cell distribution according to the signal intensity of phosphorus in the control, and determining the proportion of cells distributed as cells having higher signal intensity of phosphorus in the sample.

In an embodiment, in a case where the control contains normal cells, the cell analysis method may further include a step of determining whether measurements of the signal intensity of phosphorus measured from respective cells include a range in which measurements detected in the sample are higher than the range of measurements detected in the normal cells, that is, a step of determining whether the signal intensity of phosphorus detected in the sample is higher than the signal intensity of phosphorus of the normal DNA doubling.

In an embodiment, histograms of relative quantitative value of phosphorus for each cell nucleus are obtained in cells of a cancer suspected specimen as a sample and normal cells derived from the same organ or cell population as a control. The signal intensity distribution of phosphorus of the cancer suspected specimen and the signal intensity distribution of phosphorus of the normal cell derived from the same organ or cell population may be compared, and the difference between the signal intensity distributions may be determined.

Also, the intensity distribution of a cancer suspected specimen as a sample, the intensity distribution of normal cells derived from the same organ or cell population as a control, and the difference between the intensity distributions may be compared with the intensity distribution of the phosphorus amount of normal cells derived from an organ or cell population, the intensity distribution of the phosphorus amount of cancer cells derived from an organ or cancer cell population, and the difference between the intensity distributions registered in a database as a control.

In an embodiment, in a case where the control contains normal cells, the cell analysis method may further include a step of determining the proportion of cells having higher signal intensity of phosphorus than the signal intensity of phosphorus of the control and the range of the signal intensity of phosphorus, or a step of determining cells or a region of cells having higher concentration ratio of phosphorus:sulfur than a concentration ratio of the control.

In an embodiment, in a case where the control contains normal cells, the cell analysis method may further include a step of determining the number of cells in which the concentration ratio of phosphorus and sulfur in the sample is different compared to the concentration ratio of phosphorus and sulfur in the control.

In an embodiment, in a case where the control contains normal cells, the cell analysis method may further include a step of determining the tissue distribution of cells and extracellular matrix in which the concentration ratio of phosphorus and sulfur in the sample is different compared to the concentration ratio of phosphorus and sulfur in the control.

In an embodiment, the concentration ratio of phosphorus and sulfur may be determined in cells, a cell population, or a continuous tissue containing cells and extracellular components such as extracellular matrix of a cancer suspected specimen as a sample and normal cells, a normal cell population, or a continuous tissue containing normal cells and extracellular components such as extracellular matrix as a control. The concentration ratio of phosphorus and sulfur in a cancer suspected specimen and the concentration ratio of phosphorus and sulfur of normal cells derived from the same organ or cell population may be compared, and the difference between the concentration ratios may be determined.

Furthermore, in the cell analysis method of the present disclosure, a step of staining a sample and acquiring an optical microscope image of the sample and a step of acquiring a scanning electron microscope (SEM) image of the sample may both be performed. In the acquired SEM image, cells may be highlighted based on the measured signal intensity of phosphorus or the concentration ratio of phosphorus and sulfur. Alternatively, the acquired SEM image may be collated with the optical microscope image, and in the optical microscope image, cells may be highlighted based on the measured signal intensity of phosphorus (bottom right in FIG. 2) or the concentration ratio of phosphorus and sulfur (bottom right in FIG. 3). Such a display may help visual understanding of the proliferating activity or malignancy of the cell.

Proliferating cells repeat DNA replication and cell division. The process thereof is divided into a G1 phase before DNA synthesis, an S phase where DNA is synthesized, a G2 phase before cell division, and an M phase where cells are divided, and the G1, S, G2, M phases are repeated. Meanwhile, mature cells, which are not divided, are in a G0 phase (right side in FIG. 2).

The amount of DNA contained in a cell in the G0/G1 phase is constant depending on the species, the DNA amount in the G2/M phase before division is relatively doubled. In the cells of S phase where DNA is being synthesized, DNA in an amount between the DNA amounts in these phases is present. Since the start of DNA synthesis is determined before the S phase, a cell population which is not divided is in the G0 phase, a cell population whose proliferation is slow contains many cells in the G0/G1 phase, and a cell population whose proliferation is rapid, such as a cancer tissue relatively contains many cells in the S, G2, and M phase. For this reason, in the cell population, the ratio of the number of cells containing DNA in the DNA amount of the G0/G1 phase and the number of cells containing DNA in an amount larger than this amount is an indicator for determining the proliferating activity of the cell.

Also, in cancer, cells in which the DNA amount per one cell abnormally increase due to abnormal division are generated apart from the DNA synthesis before cell division. In such a cell, DNA in an amount several times the DNA amount of normal cells is present in some cases. Thus, abnormal increase in the DNA amount is also an indicator for determining the malignancy or cancer.

Since one phosphorus atom is bound per one base of DNA, the number of phosphorus atoms derived from DNA proportionally increase in the DNA synthesis process before cell division. In light of this, in the cell analysis method of the present disclosure, the difference in the phosphorus amount of each cell or cell nucleus contained in the sample is measured, and the relative difference in the DNA amount for each cell or cell nucleus is quantitatively detected. By calculating the DNA amount from the phosphorus amount in the cell or cell nucleus, the proliferating activity of cells and the malignancy of cells contained in the sample can be analyzed.

There is a tendency that cytoplasm develops in normal cells or cells having low division activity in comparison with cancer cells having high proliferating activity and repeating division. Therefore, for the amount ratio of the nucleus and cytoplasm per cell, there is a tendency that the ratio of the nucleus is high in cells having high proliferating activity, whereas the ratio of the cytoplasm is high in normal cells. Accordingly, the ratio of the nucleus and cytoplasm may be one of the indicators for cancer cell identification.

When the amount of phosphorus which is an element contained in a large amount in DNA and the amount of sulfur derived from protein and the like are compared, the ratio of phosphorus:sulfur in the nucleus may be higher than the ratio of phosphorus:sulfur in the cytoplasm because phosphorus derived from DNA is contained in the nucleus. For this reason, when the concentration ratio of phosphorus and sulfur in the entire cell is measured, the ratio of phosphorus per cell may be higher in cancer cells, in which the amount ratio of the nucleus per cell is high, than in normal cells. The concentration ratio of phosphorus and sulfur reflects the ratio of the nucleus and cytoplasm, and thus allows analysis of the proliferating activity of cells and the malignancy of cells.

The extracellular matrix, which forms a tissue, has many S—S bonds in collagen and others, sulfated polysaccharide, and the like, and thus relatively contains sulfur. Therefore, the concentration ratio of phosphorus and sulfur in the tissue is an indicator for determining the abundance of cells having high proliferating activity in the tissue.

It is also possible to determine whether the sample contains cancer cells from the proliferating activity of cells or the malignancy of cells contained in the sample. In a case where the sample contains cancer cells, it is also possible to determine whether the cancer cells have high malignancy. Thus, the cell analysis method of the present disclosure can be used for assisting a diagnostic method of cancer and a method of determining cancer malignancy.

With the cell analysis method of the present disclosure, it is possible to analyze the proliferating activity and malignancy of cells contained in the sample rapidly and highly accurately. Furthermore, it is possible to quantitatively determine whether cells contained in the sample contain cancer cells.

In another aspect, the cell analysis apparatus of the present disclosure may include:

an element analysis unit that is configured to measure a signal intensity of phosphorus or signal intensities of phosphorus and sulfur by electron beam or X-ray irradiation elemental analysis;

a database to which a signal intensity of phosphorus of a control, or signal intensities of phosphorus and sulfur or a concentration ratio of phosphorus and sulfur of a control is registered; and a comparison unit that is configured to compare a cell distribution according to the signal intensity of phosphorus measured in the element analysis unit with a cell distribution according to the signal intensity of phosphorus of the control registered in the database, or a comparison unit that is configured to compare a concentration ratio of phosphorus and sulfur calculated from the signal intensities of phosphorus and sulfur measured in the element analysis unit with the concentration ratio of phosphorus and sulfur of the control registered in the database.

FIG. 1 illustrates a configuration example of a cell analysis apparatus of the present disclosure. The element analysis unit is not particularly limited as long as it is an apparatus that can perform electron beam or X-ray irradiation elemental analysis described above. For example, the element analysis unit includes an electron beam or X-ray irradiation unit, and an X-ray detection unit. As the X-ray detection unit, an apparatus including an energy dispersive X-ray spectroscope (EDS), a wavelength-dispersive X-ray spectroscope (WDS), or an X-ray microscope can be used.

The comparison unit can be a device or apparatus that is configured to generate a cell distribution from the signal intensity of phosphorus obtained from the element analysis unit (in some cases, the signal intensity of phosphorus calculated in a calculation unit), and compare the cell distribution with the cell distribution of signal intensity of phosphorus of the control registered in the database.

In addition, the comparison unit can be a device or apparatus that is configured to calculate the concentration ratio of phosphorus and sulfur calculated from the signal intensities of phosphorus and sulfur measured in the element analysis unit (in some cases, the mass concentration ratio of phosphorus and sulfur calculated in the calculation unit), and compare the concentration ratio with the concentration ratio of phosphorus and sulfur of the control registered in the database.

For example, a computer can be used as the comparison unit by being controlled or externally controlled with an appropriate software.

Also, as the database, databases known in the technical field can be used. For example, a database that is stored in the memory unit of a computer, a database that is recorded in a readable recording medium (CD-ROM and the like), a database that can be accessed through the Internet, and the like can be used. Information registered in the database may be, although not limited thereto, the signal intensity of phosphorus, and/or the signal intensities of phosphorus and sulfur or the concentration ratio of phosphorus and sulfur of at least one type of cell selected from the group consisting of normal cells, malignant cells, cells having high proliferating activity, and cells exhibiting abnormal DNA increase. For example, the signal intensity of phosphorus, and/or the signal intensities of phosphorus and sulfur or the concentration ratio of phosphorus and sulfur of a normal tissue in a given site and cells of a cancer tissue of the same site are registered in the database.

The cell analysis apparatus of the present disclosure may further include an image acquisition unit that is configured to acquire an image of the sample. As the image acquisition unit, any device or apparatus that is configured to acquire an image useful for analysis of the proliferating activity or malignancy of cells can be used. For example, as such an image acquisition unit, a scanning electron microscope (SEM) and an optical microscope can be used, or both microscopes can be used in combination.

The cell analysis apparatus of the present disclosure may further include an output unit that is configured to output the comparison result in the comparison unit, or may be connected to such an output unit. As the output unit, a device or apparatus known in the technical field can be used as long as it can output the result of the comparison unit. For example, a display unit that visually outputs the result (display, printer, and the like), or a voice unit that auditorily outputs the result (such as a speaker unit) can be used. The output unit may be the constitutional element of the cell analysis apparatus, or may be connected to the cell analysis apparatus from the outside.

By using the cell analysis apparatus of the present disclosure, it becomes possible to analyze the proliferating activity or malignancy of cells simply, rapidly, and highly accurately, thus enabling easy determination of cancer. Thus, the cell analysis apparatus of the present disclosure can also be used as a cancer diagnostic apparatus.

Hereinafter, the specific embodiments of the present invention will be described in the Examples, but the present invention is not limited to the following Examples.

Example 1

As the Example of the present invention, normal human mesenchymal stem cells (hMSC) having low proliferating activity and human cancer cells (HeLa cells) having high proliferating activity were tested, for example. The type of the cell to be used is not limited to these cells.

A cover glass which has been subjected to a cell adhesion treatment was immersed on the bottom surface of a cell culture dish, and then cells were seeded, thus subjecting cells to adhesive culture on the cover glass. When the cells were reached sub-confluent, the cover glass was removed, immersed in alcohol or the like to fix the cells adhered to the cover glass. In order to easily identify the position of the cell nucleus in observation, nuclear staining was performed with a staining solution not containing phosphorus, such as hematoxylin, as necessary, and then the cells were dried.

The cover glass to which the dried cells have been adhered was placed on the sample holder of a scanning electron microscope (SEM), the sample holder was inserted in a sample chamber, and then the sample chamber was evacuated. The cells were observed at an observation magnification of 1,000, and an SEM image was acquired. Note that the magnification is not limited thereto. Subsequently, the region of the cell nucleus in the acquired SEM image was selected, and the fluorescent X-ray of phosphorus was measured by energy dispersive X-ray spectrometry (EDX). In the cell analysis method, the signal intensity of phosphorus in the entire cell may be measured, but phospholipid and other molecules containing phosphorus other than DNA are present in the cell. Thus, by selecting the nuclear region in the SEM image, the difference in the phosphorus amount according to the difference in the DNA amount for each cell nucleus can be detected more accurately.

Figure 4A:
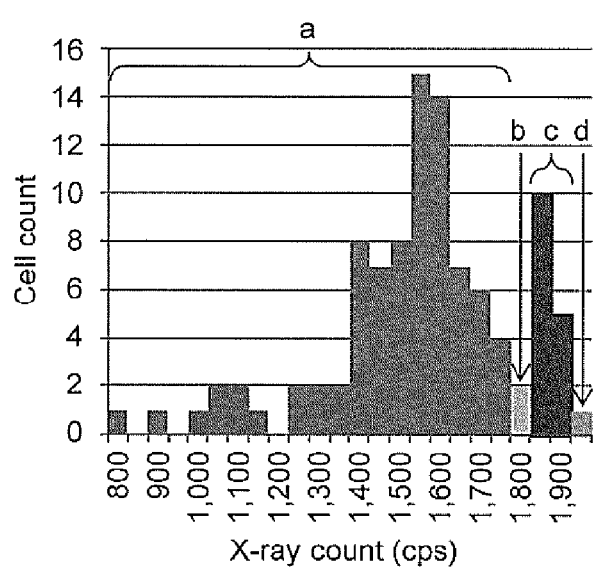
FIGS. 4A to 4D show examples of the histograms (FIG. 4A and FIG. 4C) in which the phosphorus X-ray signal intensity of cultured cells is measured by the cell analysis method and examples of the histograms (FIG. 4B and FIG. 4D) in which the DNA fluorescence intensity is simultaneously measured by flow cytometry.
Figure 4B:
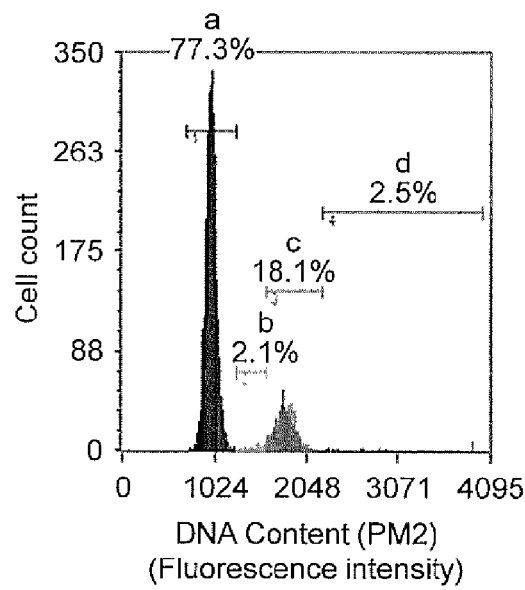
Figure 4C:
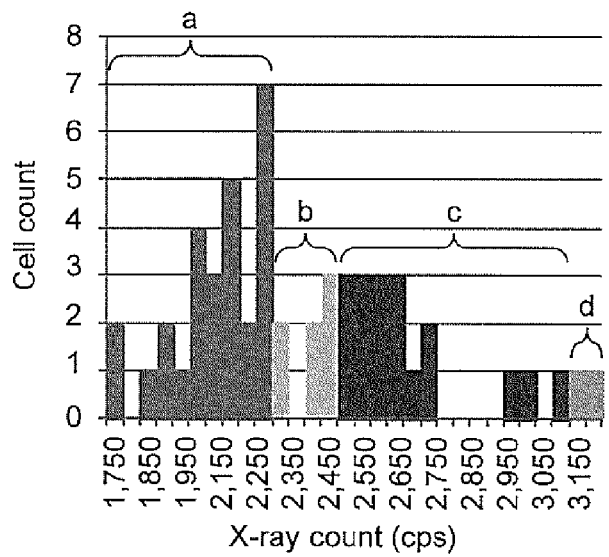

Cell nuclei of from 50 to 100 cells randomly selected from a large number of cells adhered on the cover glass were measured by EDX, and the cell distribution according to the X-ray signal intensity of phosphorus was displayed with histograms (FIGS. 4A and 4C). Note that the number of cells is not limited thereto.

The distribution was roughly divided into two, and it was indicated that, in cells having low proliferating activity (hMSC), the proportion of the group of cells having small X-ray signal intensity of phosphorus was high (FIG. 4A), whereas in cells having high cell proliferating activity (HeLa cells), the proportion of the group of cells having high intensity was relatively high (FIG. 4C). Also, in cancer cells (HeLa cells), the proportion of cells having higher X-ray signal intensity of phosphorus than the signal intensity of the G2/M phase was higher than the proportion of normal cells (hMSC).

Cells adhered to the bottom surface of the dish from which the cover glass has been removed were removed from bottom surface of the dish by a trypsinization and collected. Cells were stained with fluorescent dyes which bind to DNA, and the fluorescence intensity was measured using flow cytometry. Then, the distribution of the fluorescence intensity was displayed with a histogram. In the flow cytometry, the fluorescence intensity for 5,000 cells was measured.

Figure 4D:
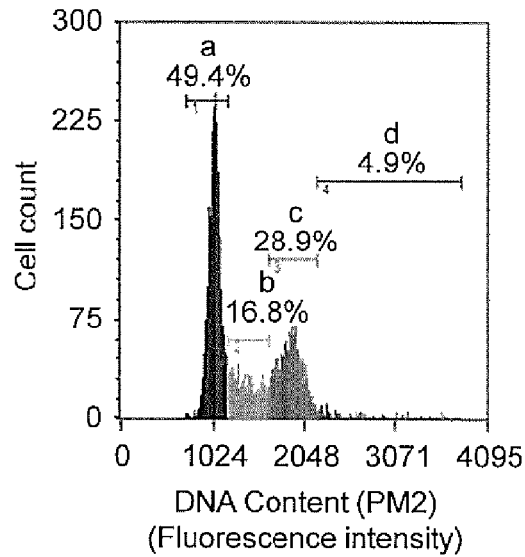

In the cells measured by flow cytometry, the distribution was roughly divided into two, and it was indicated that, in cells having low proliferating activity (hMSC), the proportion of the group of cells having small fluorescence intensity was high (FIG. 4B), whereas in cells having high cell proliferating activity (HeLa cells), the proportion of the group of cells having high fluorescence intensity was relatively high (FIG. 4D). Also, in cancer cells (HeLa cells), the proportion of cells having higher fluorescence intensity of phosphorus than the fluorescence intensity of the G2/M phase was higher than the proportion of normal cells (hMSC).

The proportion of distribution of the X-ray signal intensity measurement of phosphorus by EDX and the proportion of the distribution of fluorescence intensity measurement by the flow cytometry were similar. According to the present invention, it is possible to quantitatively determine the proportion of cells having different DNA amounts in a cell population by measuring the X-ray signal intensity of phosphorus. Thought this measurement, it became possible to determine the proliferating activity and abnormal DNA increase in the cell population.

In isolated cells, such as isolated culture cells, it is possible to determine the proliferating activity of cells by measuring the difference in the DNA amount per cell by at least these two types of methods. In the measurement of the X-ray signal intensity of phosphorus using EDX according to the present invention, it becomes possible to measure the difference in DNA amount using a smaller number of cells.

Example 2

Cancer cells continue to proliferate due to cell division, but in contrast, mature normal cells stop division, or in organs of which metabolism of cells are active, somatic stem cells and precursor cells are normally divided. Therefore, the presence of cell clusters disorderly proliferating in a specimen tissue is an indicator for determining the cancer tissue.

A tissue section containing both a cancer suspected tissue and a normal tissue adjacent to the cancer suspected tissue, or a tissue section of a cancer suspected tissue and a tissue section of a normal tissue of the same organ, which has been separately collected were prepared, and allowed to adhere to a supporting substrate such as a slide glass. In order to easily identify the position of the nucleus, the nucleus was stained if necessary with a hematoxylin staining solution not containing phosphorus or sulfur, and the like, followed by drying.

A tissue section adjacent to the cancer suspected tissue section was stained by hematoxylin-eosin staining which is performed in normal pathological examination, sealed with a cover glass, and then observed by an optical microscope. Thus, a region exhibiting disordered proliferation and abnormal morphology due to damage caused by such uncontrolled proliferation in the tissue was identified. Note that since it is possible to confirm the tissue structure with the above section stained with hematoxylin by using an optical microscope or an SEM, hematoxylin-eosin staining of the continuous section is not essential.

Since the morphology of the cancer tissue is not uniform, a region to be subjected to elemental analysis of phosphorus or elemental analysis of phosphorus and sulfur is selected based on the information of the morphology obtained in the observation previously performed. It may be desirable to exclude blood cells in a vessel, lymphocytes and necrotic regions found in inflammatory areas as cells to be analyzed.

A slide glass to which a tissue section containing the cancer suspected tissue has been adhered was placed on a sample holder of an SEM, and the sample holder was inserted in the sample chamber, and then the sample chamber was evacuated. The section was observed at an observation magnification of 600, and thus an SEM image of the region to perform elemental analysis selected above was acquired. Note that the magnification is not limited thereto.

Subsequently, in a case of detecting phosphorus per the cell nucleus, a region of the cell nucleus in the acquired SEM image was selected, and the fluorescent X-ray of phosphorus was measured by EDX.

A normal tissue adjacent to the cancer suspected tissue or the tissue section of normal cells of the same organ was observed by the SEM using the same procedure, then a region of the cell nuclei in the acquired SEM image was selected, and the fluorescent X-ray of phosphorus was measured by EDX.

Phospholipid and other molecules containing phosphorus other than DNA are present in the cell. Thus, by selecting the nuclear region in the SEM image, the difference in the phosphorus amount according to the difference in the DNA amount for each cell nucleus can be detected more accurately.

Cell nuclei of from 50 to 100 cells randomly selected were measured for each of the cancer suspected tissue and the normal tissue, and the cell distribution according to the X-ray signal intensity of phosphorus was displayed with histograms. Note that the number of cells is not limited thereto.

In cells of the cancer suspected tissue and normal cells derived from the same organ, histograms of the relative quantitative value of phosphorus for each cell nucleus were obtained.

In the comparison unit, the intensity distribution of cells of the cancer suspected tissue and the intensity distribution of normal cells derived from the same organ were compared, and the difference between the intensity distributions was determined.

Also, in the comparison unit, the intensity distribution of the cancer suspected specimen, the intensity distribution of normal cells adjacent to the specimen, and the difference between the intensity distributions were compared with the intensity distribution of the phosphorus amount of the normal cells derived from an organ of the same species as the specimen, the intensity distribution of the phosphorus amount of cancer cells derived from an organ of the same species as the specimen, and the difference between the intensity distributions, which have been registered in the database. Thereby, it was determined whether the target specimen was cancer.

In a case of calculating the concentration ratio of phosphorus and sulfur based on the measured signal intensities of phosphorus and sulfur, the cancer suspected tissues were selected from the acquired SEM images of a tissue A where the proportion of the nucleus in the cell is relatively low and a tissue B where the proportion of the nucleus in the cell is relatively high, and the fluorescent X-ray of phosphorus and sulfur was measured by EDX (FIG. 5).

An area of the cancer suspected tissue was measured, and the mass concentration was calculated from the X-ray signal intensities of phosphorus and sulfur, and illustrated (FIG. 5). In the tissue A where the proportion of the nucleus in the cell is relatively low, the mass concentration of phosphorus and sulfur was approximately the same, and the concentration ratio was similar to that of the interstitium. In contrast, in the tissue B where the proportion of the nucleus in the cell is relatively high, it was indicated that the mass concentration of phosphorus was high.

In a sample like a tissue section, composed of a plurality of cells and extracellular matrix, it becomes possible to measure the difference in the proportion of the nucleus, cytoplasm, and extracellular matrix in the tissue directly and rapidly compared to the conventional staining method, by determining the concentration ratio of phosphorus and sulfur by measurement of the X-ray signal intensity of phosphorus using EDX according to the present invention.

Example 3

Cells collected from the surface of a tissue with a brush or the like in endoscopy were placed on a slide glass, the slide glass was immersed in alcohol to fix the cells. Cells were stained by using a May-Giemsa staining solution and the like, and then cells were dried, the morphology information of the cell was obtained by optical microscope observation.

The cover glass to which the dried cells have been adhered was placed on the sample holder on the SEM, the sample holder was inserted in a sample chamber, and then the sample chamber was evacuated. The cells were observed at an observation magnification of 1,000, and an SEM image was acquired. Note that the magnification is not limited thereto. Since cells are not uniform, it may be desirable to select cells to be subjected to elemental analysis of phosphorus based on the morphology information obtained in the previous optical microscope observation and exclude hemocytes as cells to be analyzed.

The region of the cell nucleus was selected in the acquired SEM image, and the fluorescent X-ray of phosphorus was measured by EDX. Cell nuclei of from 50 to 100 cells randomly selected were measured, and the cell distribution according to the X-ray signal intensity of phosphorus was displayed with a histogram. Note that the number of cells is not limited thereto.

In the comparison unit, the cell distribution according to the measured X-ray signal intensity of phosphorus of cells was compared with the intensity distribution of the phosphorus amount of normal cells derived from an organ of the same species as the specimen and the intensity distribution of the phosphorus amount of cancer cells derived from an organ or cancer cell population of the same species as the specimen which have been registered in the database. Thereby, it was determined whether the target specimen was cancer.

The invention claimed is:

1. A method for analyzing a proliferating activity or malignancy of a cell, the method comprising:
   acquiring a scanning electron microscope (SEM) image of a sample containing a plurality of cells;
   selecting a nucleus region of each of the plurality of cells from the SEM image;
   measuring a signal intensity of phosphorus in the nucleus region of each of the plurality of cells by electron beam or X-ray irradiation elemental analysis; and
   determining a cell distribution by comparing the signal intensity of the phosphorus in the nucleus region of each of the plurality of cells to a respective signal intensity of a control.

2. The method according to claim 1, wherein the sample is a tissue section or cells adhered to a supporting substrate.

3. The method according to claim 1, wherein the plurality of cells are derived from an organ or a cell population.

4. The method according to claim 1, wherein the control comprises at least one type selected from the group consisting of a normal cell, a malignant cell, a cell having high proliferating activity, or a cell exhibiting abnormal DNA increase.

5. The method according to claim 1, wherein in a case where the control contains a normal cell, the method further comprises:
   determining a proportion of plurality of the cells that have higher signal intensity of the phosphorus than the respective signal intensity of the phosphorus of the control and a range of the signal intensity of the phosphorus.

6. The method according to claim 1, further comprising:
   staining the sample and observing the sample by an optical microscope before acquiring the SEM image.

7. The method according to claim 1, further comprising:
   staining the sample and acquiring an optical microscope image;
   highlighting a particular cell among the plurality of cells in the SEM image based on the measured signal intensity of the phosphorus; and
   collating the SEM image with the optical microscope image, and
   highlighting the particular cell among the plurality of cells in the optical microscope image based on the measured signal intensity of the phosphorus.

8. The method according to claim 1, further comprising determining whether the plurality of cells comprises a cancer cell.

9. The method according to claim 1, wherein in a case where the control contains a normal cell, the method further comprises:
   determining one or more cells among the plurality of cells or a region of the plurality of the cells having higher concentration ratio of phosphorus:sulfur than a concentration ratio of the control.

10. The method according to claim 1, further comprising:
    staining the sample and acquiring an optical microscope image;
    highlighting a particular cell among the plurality of cells in the SEM image based on a calculated concentration ratio of the phosphorus and sulfur; and
    collating the SEM image with the optical microscope image, and highlighting the particular cell among the plurality of cells in the optical microscope image based on the calculated concentration ratio of phosphorus and sulfur.

11. The method according to claim 1, further comprising:
    determining a cell distribution based on the signal intensity of phosphorus; and
    displaying the cell distribution as a histogram, SEM image and optical microscope image.

12. An apparatus for analyzing a proliferating activity or malignancy of a cell, the apparatus comprising:
    an element analysis unit that is configured to measure a signal intensity of phosphorus by electron beam or X-ray irradiation elemental analysis;
    a database that stores of a control signal intensity of the phosphorus of a control; and
    a processor that is communicatively coupled to the element analysis unit and the database, wherein the processor is configured to:
    acquire a scanning electron microscope (SEM) image of a sample containing a plurality of cells,
    receive a selection a nucleus region of each of the plurality of cells from the SEM image;
    determine a cell distribution by comparing the signal intensity of the phosphorus the nucleus region of each of the plurality of cells to the control signal intensity of the phosphorus of the control.

13. The apparatus according to claim 12, wherein the element analysis unit comprises an energy dispersive X-ray spectroscope (EDS), a wavelength-dispersive X-ray spectroscope (WDS), or an X-ray microscope.

14. The apparatus according to claim 12, wherein the sample is a tissue section or cells adhered to a supporting substrate.

15. The apparatus according to claim 12, wherein the plurality of cells are derived from an organ or a cell population.

16. The apparatus according to claim 12, wherein the control comprises at least one type selected from the group consisting of a normal cell, a malignant cell, a cell having high proliferating activity, or a cell exhibiting abnormal DNA increase.

17. The apparatus according to claim 12, further comprising:
    the selection the nucleus region is selected by staining the sample and observing the sample by an optical microscope before acquiring the SEM image.

18. The apparatus according to claim 12, wherein the processor is further configured to
  determine whether the sample comprises a cancer cell.

* * * * *